(12) United States Patent
Hientzsch et al.

(10) Patent No.: US 10,405,904 B2
(45) Date of Patent: Sep. 10, 2019

(54) CANNULATED BONE SCREW

(71) Applicant: ARTHREX, INC., Naples, FL (US)

(72) Inventors: Marcus Hientzsch, Dachau (DE);
Gerlinde Michel, Munich (DE);
Markus Scheibel, Berlin (DE)

(73) Assignee: ARTHREX, INC., Naples, FL (US)

( * ) Notice: Subject to any disclaimer, the term of this patent is extended or adjusted under 35 U.S.C. 154(b) by 667 days.

(21) Appl. No.: 15/093,124

(22) Filed: Apr. 7, 2016

(65) Prior Publication Data

US 2016/0213413 A1 Jul. 28, 2016

Related U.S. Application Data

(63) Continuation of application No. PCT/EP2014/071458, filed on Oct. 7, 2014.

(30) Foreign Application Priority Data

Oct. 7, 2013 (EP) .................................... 13187609

(51) Int. Cl.
*A61B 17/86* (2006.01)
*A61B 17/88* (2006.01)

(52) U.S. Cl.
CPC .......... *A61B 17/864* (2013.01); *A61B 17/863* (2013.01); *A61B 17/8635* (2013.01);
(Continued)

(58) Field of Classification Search
CPC . A61B 17/8635; A61B 17/864; A61B 17/863; A61B 2017/8655; F16B 25/0015; F16B 25/0026; F16B 25/103
(Continued)

(56) References Cited

U.S. PATENT DOCUMENTS 4,449,874 A * 5/1984 McKinney .......... F16B 25/0078
411/418
4,636,121 A * 1/1987 Miller ..................... F16B 39/04
411/140

(Continued)

FOREIGN PATENT DOCUMENTS

DE 202006012964 U1 10/2006
EP 2498694 9/2012
WO 2011054122 A1 5/2011

OTHER PUBLICATIONS

The Australian Examination Report for Application No. 2014333902, dated May 29, 2017.
(Continued)

*Primary Examiner* — David W Bates
(74) *Attorney, Agent, or Firm* — Carlson, Gaskey & Olds (57) ABSTRACT

An exemplary bone screw includes a proximal section including a first outer thread, a center section including a second outer thread, an unthreaded distal section on an opposite side of the center section from the proximal section, a channel extending from the proximal section to a distal opening of the unthreaded distal section, and at least one side opening extending from the channel to an outer surface of the unthreaded distal section. In some embodiments, the at least one side opening includes a cutting edge configured to cut a material as the bone screw is rotated in a direction for removing the bone screw. In other embodiments, the side opening is formed in at least one of the center section and the unthreaded distal section and includes a diameter that increases in a direction from the channel toward an outer surface of the center section or the unthread distal section. The exemplary bone screws may be used to treat bone fractures with or without a bone plate.

19 Claims, 8 Drawing Sheets

(52) U.S. Cl.
CPC ....... *A61B 17/8605* (2013.01); *A61B 17/8805* (2013.01); *A61B 2017/8655* (2013.01)

(58) Field of Classification Search
USPC ................................................ 411/395, 422
See application file for complete search history.

(56) References Cited

U.S. PATENT DOCUMENTS

| | | | | |
|---|---|---|---|---|
| 5,129,901 | A * | 7/1992 | Decoste | A61B 17/742 606/304 |
| 5,743,912 | A | 4/1998 | Lahille et al. | |
| 6,679,661 | B2 * | 1/2004 | Huang | F16B 13/002 411/178 |
| 7,338,493 | B1 * | 3/2008 | Vandewalle | A61B 17/686 606/86 A |
| 8,197,517 | B1 | 6/2012 | Lab et al. | |
| 10,188,403 | B2 * | 1/2019 | Mirochinik | A61B 17/1617 |
| 2004/0208717 | A1 * | 10/2004 | Greenhalgh | B23B 51/0018 408/224 |
| 2006/0058800 | A1 * | 3/2006 | Ainsworth | A61B 17/70 606/86 A |
| 2007/0233123 | A1 | 10/2007 | Ahmad et al. | |
| 2008/0269893 | A1 | 10/2008 | Bhatnagar et al. | |
| 2009/0018590 | A1 * | 1/2009 | Dorawa | A61B 17/864 606/301 |
| 2011/0060373 | A1 | 3/2011 | Russell et al. | |
| 2011/0213426 | A1 * | 9/2011 | Yedlicka | A61B 17/8635 606/309 |
| 2012/0053639 | A1 | 3/2012 | Grant | |
| 2012/0221062 | A1 * | 8/2012 | Wenger | A61B 17/7032 606/304 |
| 2013/0211466 | A1 * | 8/2013 | Ballard | A61B 17/8635 606/323 |
| 2014/0094859 | A1 * | 4/2014 | Reed | A61B 17/8625 606/312 |
| 2014/0135850 | A1 * | 5/2014 | Parent | A61B 17/68 606/304 |
| 2014/0257409 | A1 * | 9/2014 | Reed | A61B 17/864 606/304 |
| 2014/0277188 | A1 * | 9/2014 | Poulos | A61B 17/1655 606/304 |
| 2015/0150557 | A1 * | 6/2015 | Tsai | A61B 17/686 606/151 |

OTHER PUBLICATIONS

International Search Report and Written Opinion for International application No. PCT/EP2014/071458 dated Jan. 28, 2015.
Extended European Search Report for Application No. EP 17 20 0709 dated Mar. 19, 2018.

* cited by examiner

CANNULATED BONE SCREW

CROSS-REFERENCE TO RELATED APPLICATIONS

This application is a continuation of pending International Application No. PCT/EP2014/071458, filed on Oct. 7, 2014, which designates the United States and claims priority to European Application No. 13187609.6, filed on Oct. 7, 2013.

The entire disclosures of all of the above priority applications are incorporated herein by reference.

BACKGROUND

1. Field of the Disclosure

The disclosure relates to orthopedic devices used to reinforce bones in mammals and to a method of treating a humerus fracture. It specifically relates to cannulated bone screws and a method for using them.

2. Description of Relevant Art

Bone screws are used to reinforce bones by connecting at least two sections of a bone and/or by holding bone plates or other parts to a bone. It is often desirable to deliver medication and/or reinforcing material into the bone. A reinforcing material may be any kind of bone cement or bone graft or any other similar material. Specifically, delivery of bone cement into a bone material in close proximity of a bone screw may increase the mechanical retention of the bone screw within the bone material.

Cannulated bone screws are known from U.S. Pat. No. 6,048,343. The screw has a bore forming a central channel connected to sideward channels for delivering of bone cement into the bone surrounding the screw. A sealed adaptor is provided for connecting the screw to a dispensing device.

A further bone screw having a central channel is disclosed in U.S. Pat. No. 7,608,097 B2. A sleeve including a closed distal end can be inserted into the screw for selectively delivering a fluid to individual side holes connected to the central channel.

A further bone screw is disclosed in EP 1 210 019 B2. The screw has an inner bore connected to at least one sideward channel. The bore has a closed end so that no bone cement can penetrate through the tip of the screw.

A bone screw with a through hole and sideward openings for delivering a growth promoting agent is disclosed in US 2008/0269893. The screw is not intended to be removed from the bone. After the bone has grown into the structure of the screw, removal is impossible.

U.S. Pat. No. 8,197,517 discloses a bone screw with a blind hole and sideward openings. If cement has been introduced into the screw, removal is no longer possible.

In WO 2011/054122, a further bone screw having a blind hole and sideward openings is disclosed. The hole has inner structures or a slider to reduce the cross section and to improve distribution of material. Once cement has been introduced into the screw, removal is no longer possible.

SUMMARY

The embodiments of this disclosure are based on the object of providing a bone screw, which has a channel or lumen for the delivery of a material like medication, therapeutic fluid, or any kind of bone cement or strengthening material. The bone screw should provide an increased retention force and a decreased removal torque, which allows a removal of the screw without further damaging the bone structure. Particularly, removal of the screw should be possible after the screw has been fixed to a bone by injecting cement or a similar material through the screw into the bone or after ingrowth of bone into the screw. Another object is to provide a bone screw, which allows a selective delivery of material at selected positions of the screw. For simplifying the selective application, a specific tool is provided. Another problem to be solved is to improve a method for fastening a bone plate to a bone and/or to reinforce a bone by using a bone screw.

In a first embodiment, a bone screw has a proximal section, a center section, and an unthreaded distal section. The proximal section has an approximately cylindrical shape with a first outer thread. An outer thread is considered as a thread at the outside of the screw, basically for interfacing with a bone. In an alternate embodiment, the proximal section may have a conical shape having a first outer thread. This proximal section is intended for interfacing with a bone plate, which can be attached by means of the screw to the surface of a bone. The screw has a channel from the proximal section to the distal section, the channel defining a center axis. The screw may go through the distal section and end in a distal opening. The hollow channel is cylindrical and has a constant diameter at the center and the distal section. The diameter may be enlarged at the proximal section. The screw may also be used for fixing or holding bone parts together, without using a bone plate. Furthermore, the proximal section has at least one means for driving the screw.

Next to the proximal section is a center section. The center section has a roughly cylindrical shape and includes a second thread. The diameter of the center section is smaller than the diameter of the proximal threaded section. The pitch of the second outer thread of the center section is larger than the pitch of the first outer thread of the proximal threaded section. This difference in pitches allows for tightly fixing a bone plate to a bone or for tying at least two bone fragments together. Alternatively, both pitches may be similar. At the distal side of the second outer thread, there may be at least one cutout for simplifying cutting of the outer thread into the bone. The center section may bear at least one or a plurality of sideward holes, which allow the flow of material from the channel or lumen into the bone.

Next to the center section is a distal section. This distal section is unthreaded, has an approximately cylindrical shape, and has a centered distal opening connected to the channel of the screw for delivering material into the bone at the distal side. It may have further sideward oriented holes for delivering material into the bone. The distal section has the same diameter as the center section. It may be unthreaded. The distal section may have a closed end without a distal opening.

Within the proximal threaded section, the center section, and the distal section, a channel or lumen is provided. This channel has a circular cross section. It has a constant diameter. This channel is connected to the sideward openings and to the distal opening of the distal section. It is further connected to a proximal opening at the proximal end of the screw. The channel may be used to deliver any material, for example a bone cement (permanent or bioresorbable), or a medication into the surrounding bone material.

The side openings, which are provided in the center section and/or distal section, are provided by pairs resulting in through-holes through the screw. Therefore, two side openings are oriented at a 180° angle with respect to each other in a plane perpendicular to the center axis of the screw. In an alternative embodiment, there may be three or more side openings in the same plane. At least one opening has an elongated shape with respect to the center axis. The at least one opening may have an elliptical shape. Due to the larger extension or size of the opening parallel to the center axis, a larger total cross section of the opening can be achieved without significantly weakening the structure of the screw. There may be at least one cutting edge at at least one of the side openings. This cutting edge allows cutting of the material or bone cement when removing the screw by rotating counter-clockwise. The angle of the cutting edge is, in one embodiment, less than 90°. At least one of the side openings has a conical shape with increasing diameter towards the outside of the screw. This allows to form a cutting edge and to further increase the cross section for delivery of material into the bone. Here, the term cross section relates to the cross section available for delivery of material.

The openings may be oriented into specific directions for directing the flow of material into the bone. They are oriented orthogonally to the center axis or towards the distal end to direct the flow of material into a distal direction.

A further embodiment relates to a tool, such as a sleeve, which allows selective delivery of material into the bone surrounding the screw. The tool has a hollow shaft and a cylindrical shaft defining an inner channel for delivery of material. The outer diameter of the sleeve is adapted to fit into the channel of the bone screw. The sleeve may be inserted into different positions, which are in proximity to the distal opening or to any specific side opening to allow selective delivery of material into the surrounding bone. For precise adjustment of the insertion depth of the sleeve into the bone screw, there may be markers at the outside of the sleeve. There may be any other measuring tool for indicating the depth and/or the position of the sleeve inserted into the bone screw. The markers indicate the positions of the sleeve close to specific openings for delivering material through these openings. As there may be two openings at opposite sides of the lumen of the bone screw, the cross-section pointing outwards into the bone through the side opening is larger than the cross-section through the lumen of the bone screw. This will result in a significantly larger side flow, sideward through the side openings compared to the center flow through the remaining channel of the bone screw. This allows selective application of material to the bone. For example, material may be supplied through openings in the center section without filling the openings in the distal section. This allows the application of bone cement where needed. Such a selective application of bone cement simplifies later removal of the screw.

Another embodiment relates to a tool kit comprising at least one bone screw as described herein and at least one tool which may be a sleeve as described herein. At least one sleeve is adapted to fit into the channel of at least one screw. Furthermore, the markers at the outside of the at least one sleeve are adapted to the at least one screw.

A further embodiment relates to a method for fixing a bone screw as described herein to a bone. It includes the steps of drilling a hole into the bone, screwing the screw by rotation of the screw into the hole, inserting a sleeve into the channel of the screw, positioning of the sleeve into close proximity to at least one desired opening, and feeding a material through the sleeve via the screw into the bone. Another embodiment relates to an improved method for selectively supplying material like bone cement through a bone screw. It includes the steps of inserting a sleeve into the channel of the screw, positioning of the sleeve into close proximity to at least one desired opening, and feeding a material through the sleeve via the screw into the bone. Another embodiment relates to improving a method for fixing bone fragments and/or fixing a bone plate to a bone, such as a humerus, by fixing a screw as disclosed herein to the bone and/or the bone fragments and/or the bone plate. The process of delivering material may include the steps of delivering contrast agent for X-ray imaging, delivering of a rinsing solution, which may comprise NaCl, and finally delivering a bone cement.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but on the contrary, the intention is to cover all modifications, equivalents and alternatives falling within the spirit and scope of the present disclosure as defined by the appended claims.

DETAILED DESCRIPTION

Figure 1:
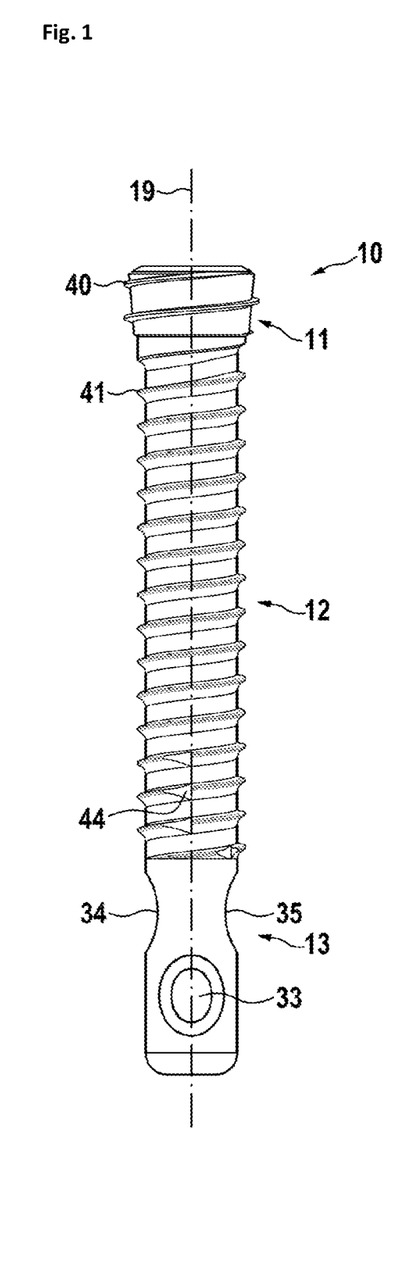
FIG. 1 shows a first embodiment of a bone screw.
Figure 16:
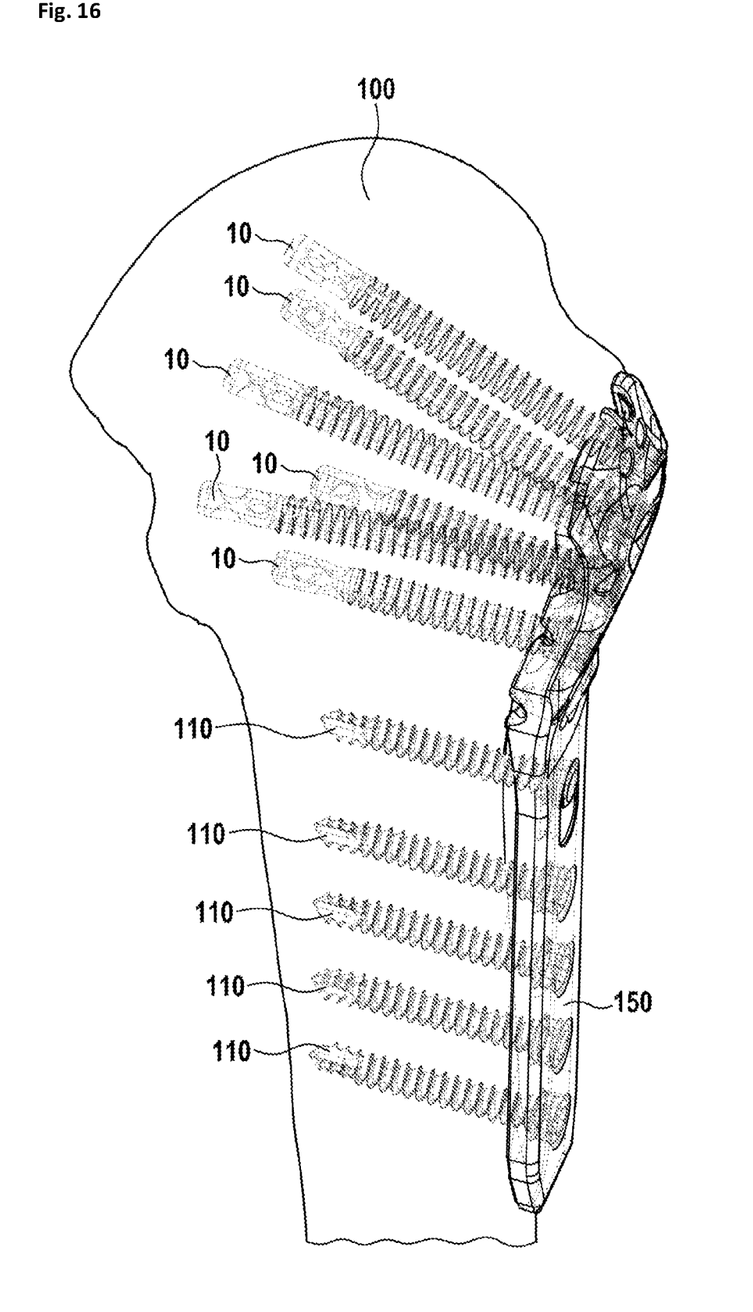
FIG. 16 shows a humerus head with a bone plate attached by the bone screws.

In FIG. 1, a first embodiment of a bone screw 10 is shown. The bone screw 10 has a threaded proximal section 11, a center section 12, and a distal section 13. The bone screw 10 further has a hollow channel 30 from the proximal section 11 through the distal section 13, defining a center axis 19. The proximal section 11 is approximately cylindrical shaped. It may also have a conical shape to simplify insertion. The proximal section 11 has a first outer thread 40, which is designed to interface with a bone plate 150 as shown in FIG. 16. The center section 12 has a cylindrical shape and is at least partially threaded with a second outer thread 41. The second outer thread 41 may have at least one cutout 44 to improve cutting of the outer thread into the bone material when inserting the screw. The pitch of the first outer thread 40 is less than the pitch of the second outer thread 41 to allow pressing of a bone plate 150 interfacing with the first outer thread 40 to a bone interfacing with the second outer thread 41. The distal section 13 is unthreaded and has at least one side opening 33, 34, 35. The side openings 33, 34, 35 have a conical shape with increasing diameters toward the outside of the bone screw 10.

Figure 2:
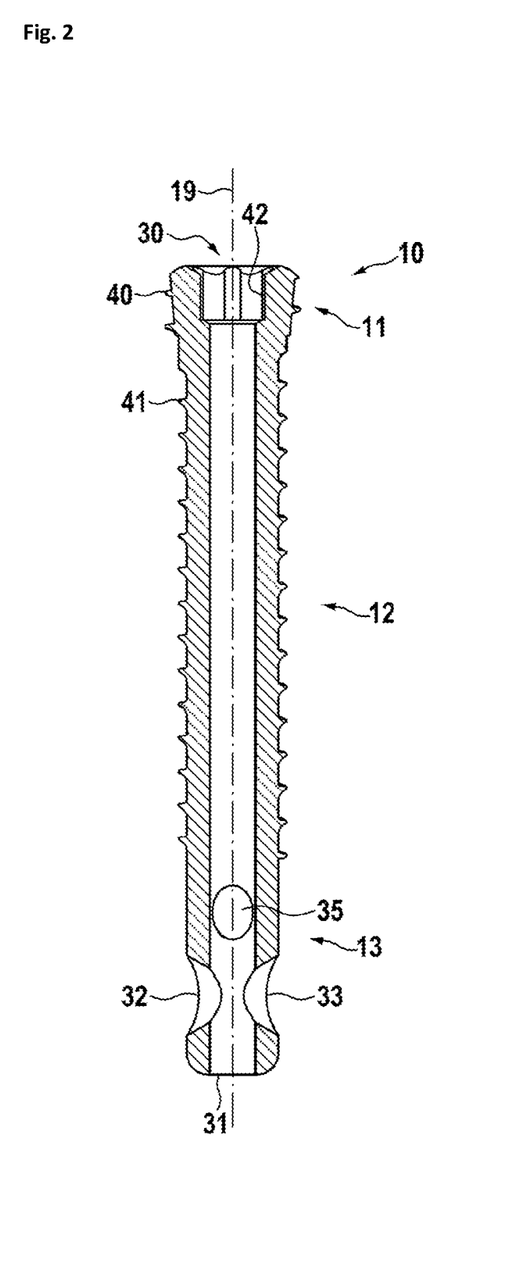
FIG. 2 shows a sectional view of the first embodiment.

In FIG. 2, a sectional view of the first embodiment is shown. The bone screw 10 has a channel or lumen 30, which proximately is centered to the center axis 19. The channel 30 passes through the proximal section 11, the center section 12, and the distal section 13. It ends with a distal opening 31 at the distal section 13. Furthermore, it is connected to at least one side opening 32, 33, 35, which may be provided in the distal section 13 or the center section 12. For rotating the screw, a means 42 for attaching a driving tool is provided for interfacing with a screwdriver, a wrench or any other tool.

Figure 3:
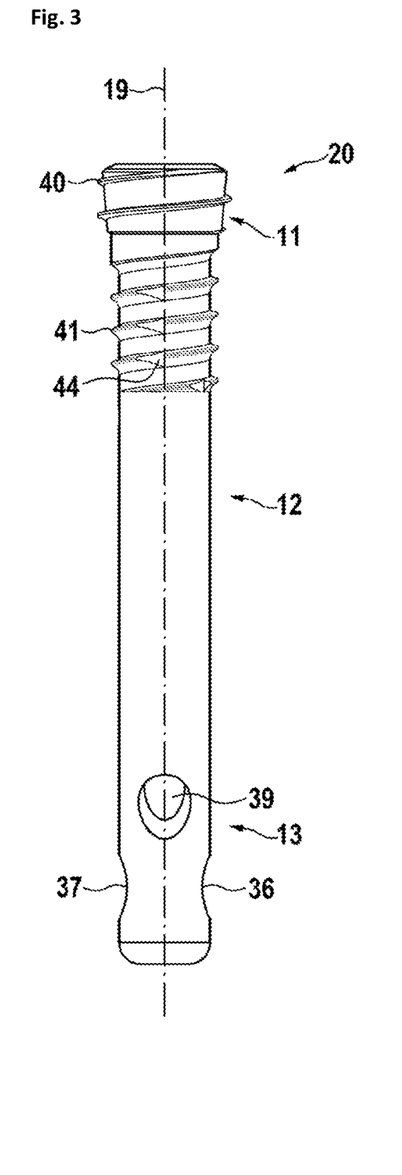
FIG. 3 shows a further embodiment of the bone screw.

In FIG. 3, a further embodiment of the bone screw 20 is shown. This screw 20 has differently shaped side openings 36, 37, 39 compared to the embodiment of FIG. 1. Here, the openings are oriented towards the distal end to direct the flow of material in a distal direction. Furthermore, the length of the second outer thread 41 is shorter than the outer thread shown in FIG. 1. Although there are preferred embodiments, any of the parts like threads or side openings shown in this document can be combined without any limitation.

Figure 4:
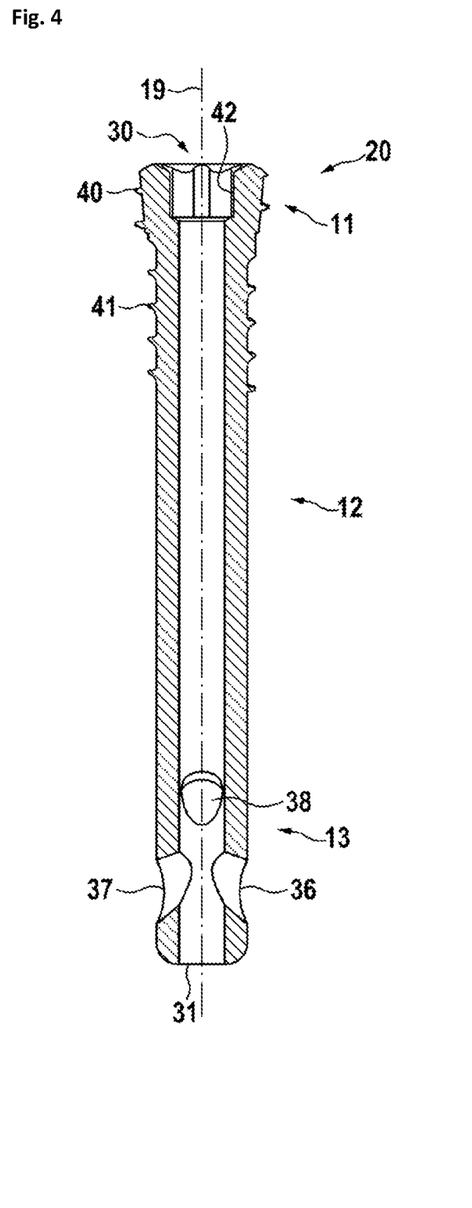
FIG. 4 shows a sectional view of the further embodiment.

In FIG. 4, a sectional view of a further embodiment of the bone screw 20 is shown. Here, the different structure of the side openings 36, 37 can be seen compared to the side openings 32, 33 of FIG. 2. The side openings shown in this figure provide a flow of material in a slightly more distal direction compared to the previous embodiment. Here a further side opening 38, which is opposing side opening 39, is shown.

Figure 5:
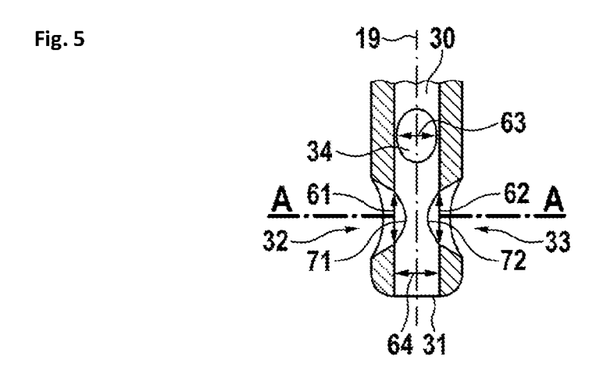
FIG. 5 shows a sectional view of the distal section of an embodiment.

In FIG. 5, a sectional view of the distal section 13 of another embodiment is shown. The first side opening 32 is located opposite to a second side opening 33. Above the side openings 32, 33, there is a further side opening 34, which basically has the same size as the other side openings, although it may have any different size.

The side openings 32, 33 have heights 61, 62. Reference sign 63 denotes the width of the channel 30, which is identical to the diameter of the distal opening 31 in this embodiment. The cross-section of two opposing side openings 32, 33 given by the heights 61, 62 and the width 63 is significantly larger than the cross-section of the channel 30 in a distal direction given by its diameter 64. This allows controlled sideward flow through the side openings 32, 33 and a minimal flow of material through the lumen 30, as will be shown later in detail.

Figure 6:
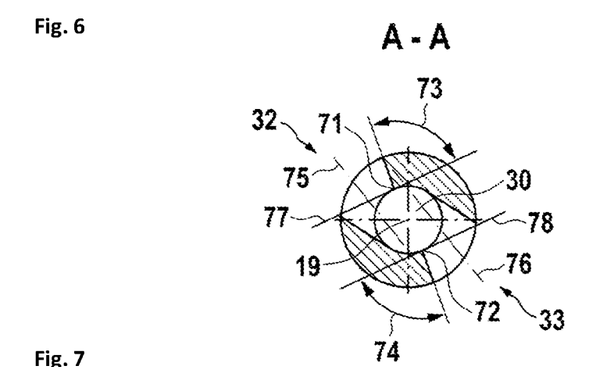
FIG. 6 shows a further sectional view of the embodiment of FIG. 5.

In FIG. 6, a further detail of section A-A of FIG. 5 is shown. The outer sides of the side openings 32, 33 form cutting edges 71, 72 which cut off the bone cement when rotating the bone screw for example for removal. These cutting edges 71, 72 significantly reduce the removal torque of the screw and help to avoid severe damage of the bone material. The angles 73, 74 of the cutting edges are less than 90° to achieve maximum cutting efficiency. In this embodiment, the cutting edges 71 and 72 are most important, as these have the first contact with the material inside the opening when rotating the screw counterclockwise for removal. Angles of less than 90 degrees may be obtained by offsetting the center axes 75, 76 of the openings 32, 33 to the center axis 19 of the screw, so that the axes do not cross. The angles 73, 74 can be defined between the tangents 77, 78 to the inner wall of the channel 30 and the leading edges of the body of the screw intersecting at the points 71, 72. This embodiment applies to a screw which has to be turned counterclockwise for removal.

Figure 7:
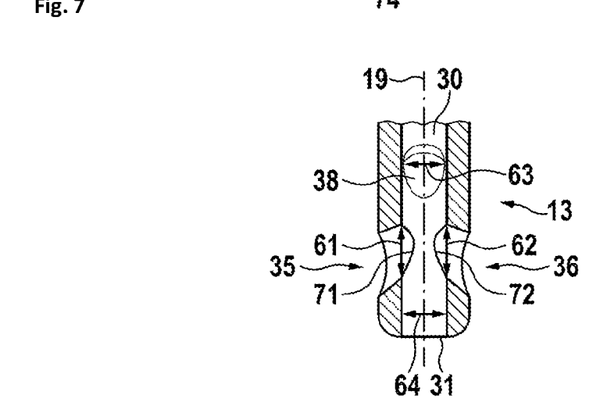
FIG. 7 shows a sectional view of the distal section of another embodiment.

In FIG. 7, a sectional view of the distal section 13 of a further embodiment is shown. Here, the side openings 35, 36, 38 have a slightly different direction. As shown before, here again, the cross-sections determined by the dimensions 61, 62, 63 of the side openings are larger than the cross-section 64 of the channel 30.

Figure 8:
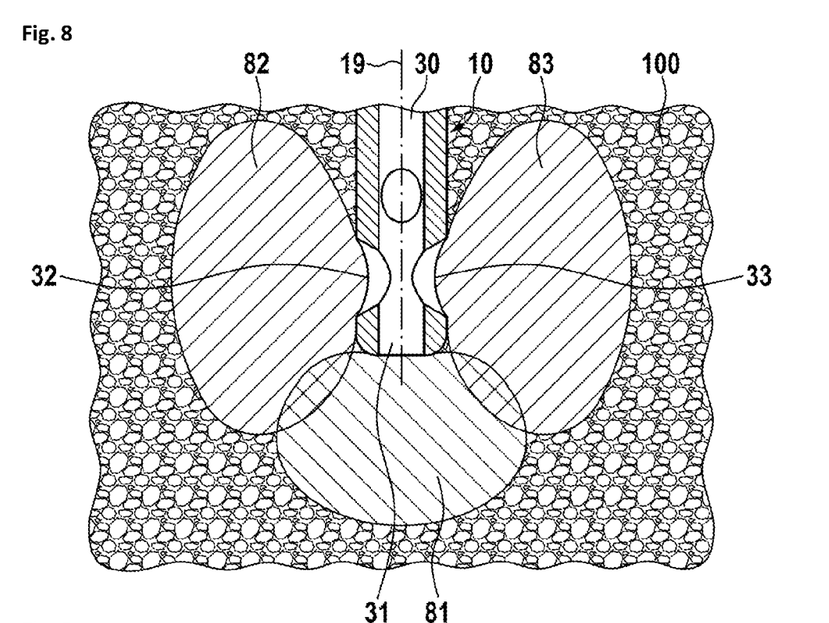
FIG. 8 shows the flow of material through the openings of the bone screw.

In FIG. 8, an example of the flow of material, like bone cement, into the bone 100 is shown. Due to the shape of the side openings 32, 33 of bone screw 10, certain areas of the bone 100 are penetrated by a material like bone cement. There is a first penetration area 81, which is supplied by the distal opening 31. A second and third penetration area 82 and 83 is supplied by the side openings 32 and 33, respectively. The penetration areas 81, 82, 83 overlap to achieve additional solidification. Due to the distal opening 31, for achieving a first central penetration area 81, an additional retention force of the bone screw can be obtained. This is significantly enlarged by connecting the penetration areas 82 and 83. It is essential that there is no outer threaded area or even a single outer thread between the side openings 32, 33 close to the distal opening and the distal opening 31 itself, as this can prevent a smooth flow of the material over the surface of the screw, specifically in a high density of the bone material. Therefore, by avoiding any outer thread, a complete enclosure of the end of the distal section and therefore a better connection to be bone 100 can be achieved. For optimized filling with material, a first material is injected through the distal opening 31 by placing a sleeve 50 as shown later in close proximity to the distal opening 31. In the next step, the sleeve 50 is slightly retracted for delivery of material through the side openings 32, 33 close to the distal opening 31.

Figure 9:
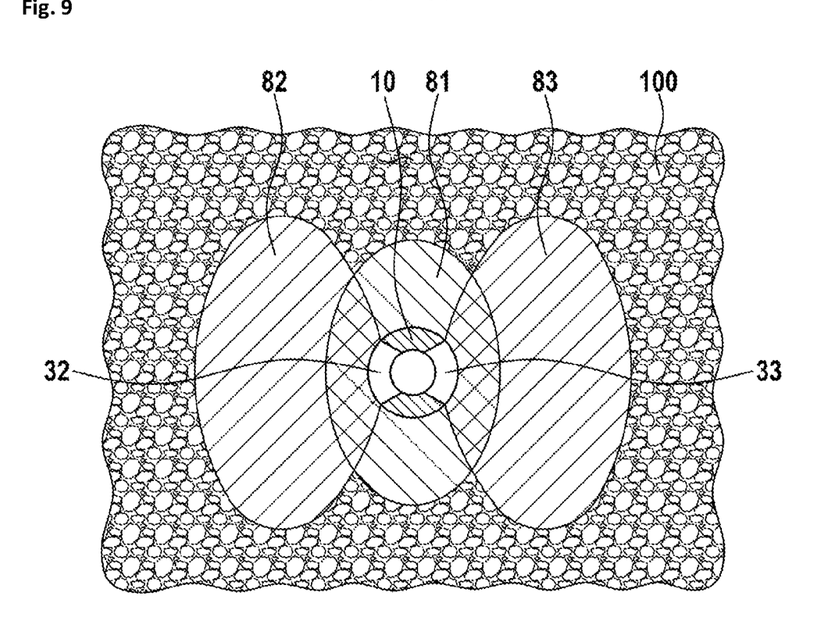
FIG. 9 shows a top view of the bone penetration areas.

In FIG. 9, a top view of the bone penetration areas 81, 82, 83 is shown. Here, the enhanced bone penetration and the connection of the penetration areas 82 and 83 by the central penetration area 81 can clearly be seen.

Figure 10:
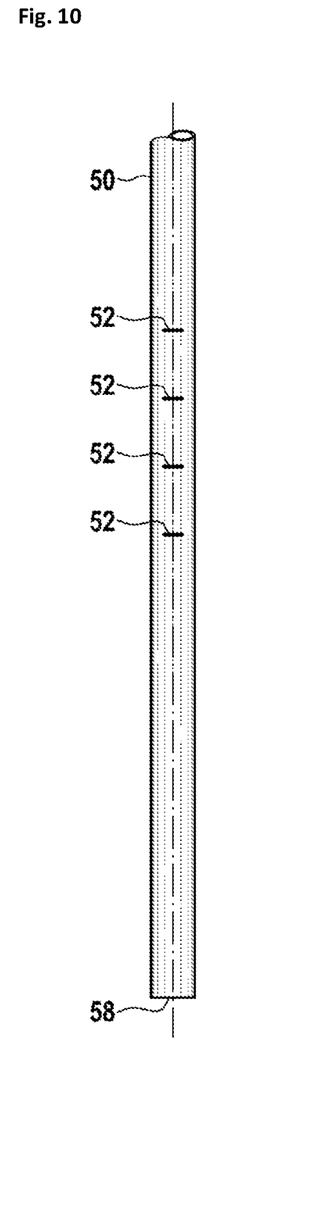
FIG. 10 shows a material feeding sleeve.

In FIG. 10, a material feeding tool like a sleeve 50 is shown. This sleeve 50 may be inserted into bone screw 10 or 20. It may bear at least one marker 52 for indicating the position of the sleeve 50 relative to the screw 10, 20 when inserted into the screw and therefore positioning the sleeve into the channel 30 of the bone screw.

Figure 11:
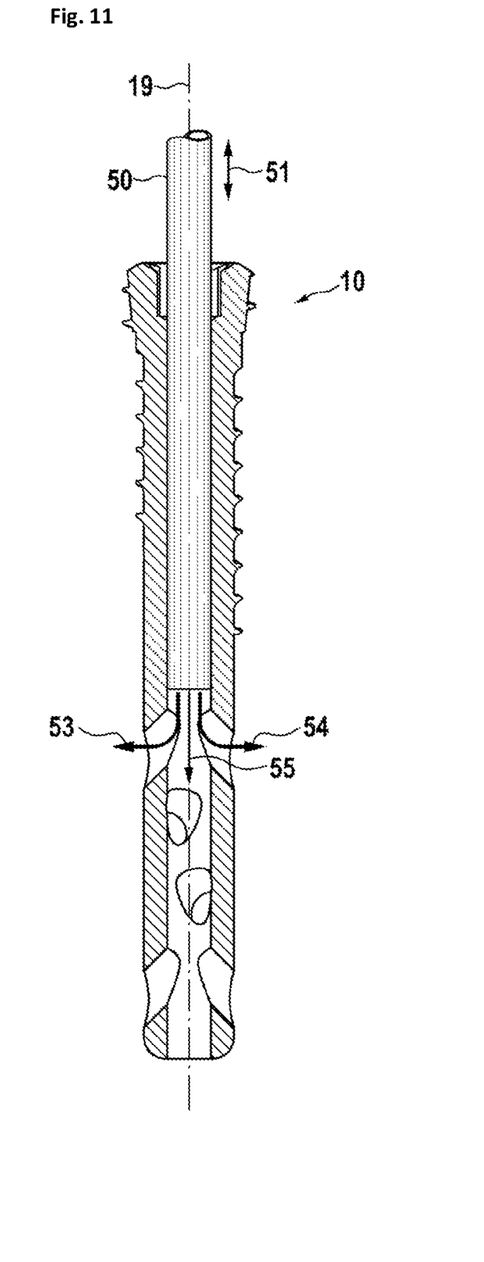
FIG. 11 shows a sleeve inserted into a bone screw.

In FIG. 11, a sleeve 50 inserted into a bone screw 10 is shown. The sleeve 50 may be moved into the direction indicated by arrow 51 and pushed into the lumen or pulled outside to place the end of the sleeve 50 at any desired position, such as close to any desired opening. By this, the flow of material may be directed through the distal opening or any side openings. The indication of the height may be given by the markers 52. Any material, such as a bone cement, may be supplied through the sleeve 50 into the bone screw 10. The flow is indicated by arrows 53, 54, 55. There are side flows 53, 54 through the side openings and a further center flow 55 into the direction of the channel 30. Due to the larger cross-section of the side openings, side flows 53 and 54 are significantly larger than the center flow 55. This allows a selective supply of material through individual side holes, where needed. An exemplary method may include first supplying bone cement through the distal section holes, and later supplying materials to remote holes in the center section. Here, other holes lying between the holes being used for supplying material to the bone may be unused. This may be the case, if there are solid bone segments and no fractured segments around the screw.

Figure 12:
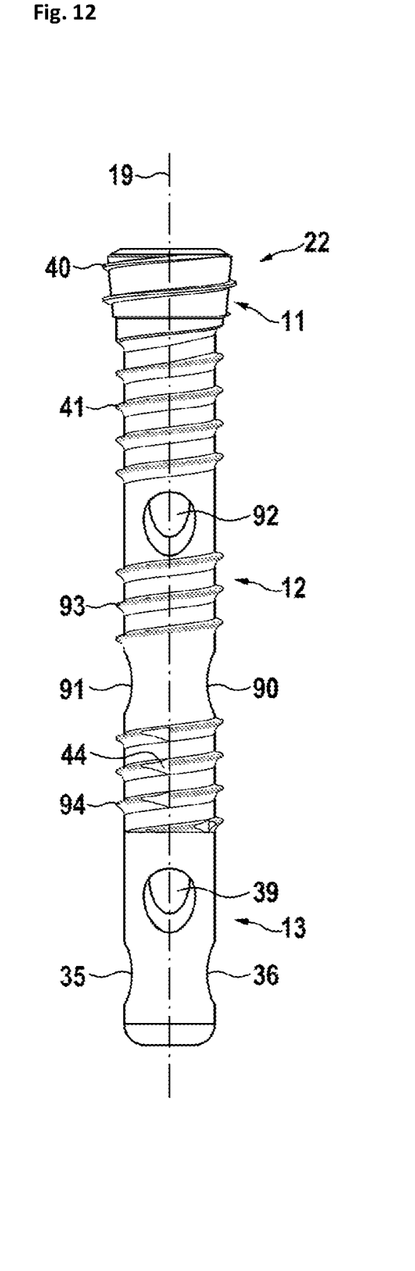
FIG. 12 shows a further embodiment of a bone screw with a plurality of side openings.

In FIG. 12, an embodiment with a plurality of side openings is shown. The proximal section 11 and the distal section 13 are similar to the embodiment of FIG. 3. The center section 12 has further side openings 90, 91 and 92. There is a further outer threaded section 93 between the side openings 92 and the side openings 90, 91. Below the latter side openings is another outer threaded section 94. There may be any combination of any one of the side openings shown in here with or without outer threaded sections in between. In general, there are only openings in unthreaded sections.

Figure 13:
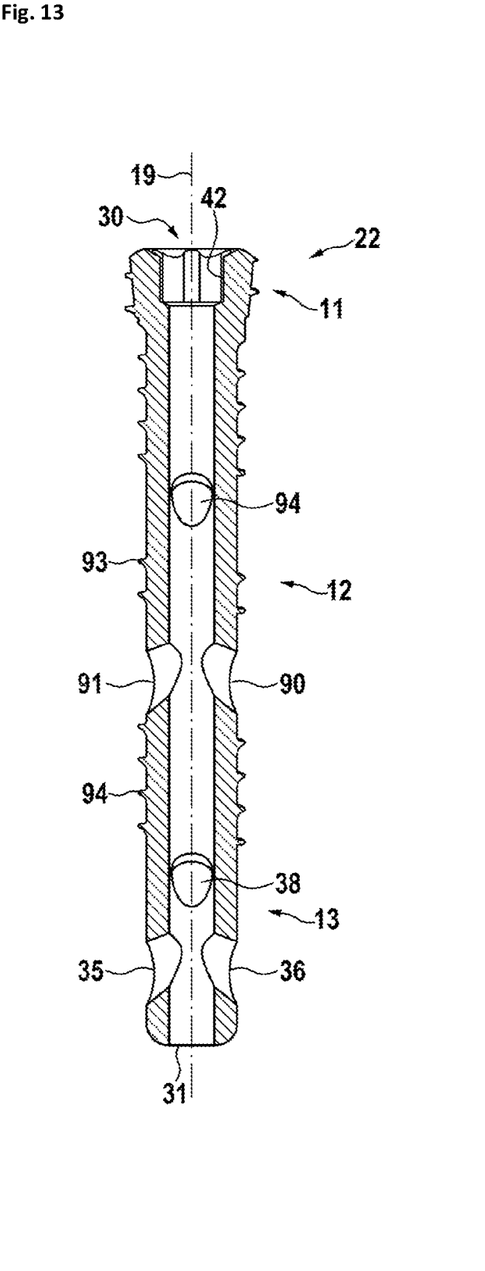
FIG. 13 shows a sectional view of the previous embodiment.

In FIG. 13, the above embodiment is shown in a sectional view. Here, a further side opening 94, which opposes side opening 92, is shown.

Figure 14:
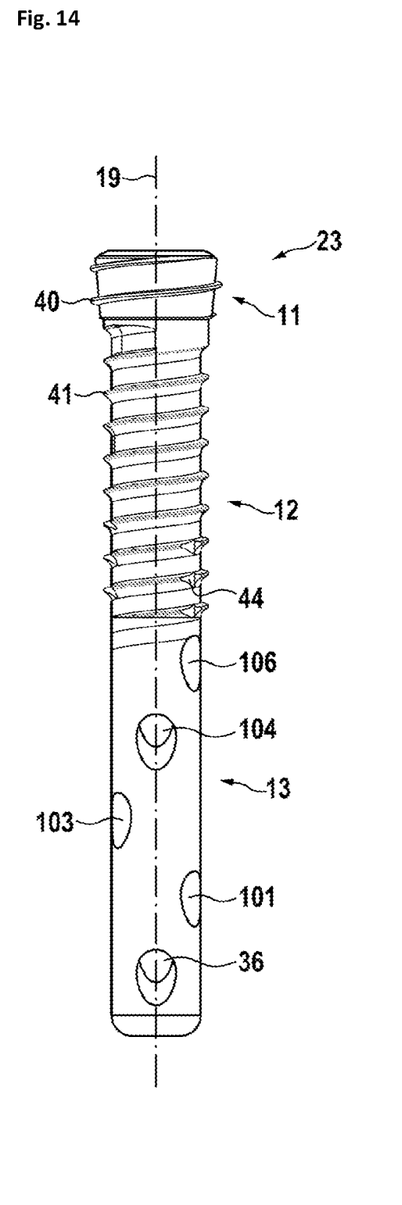
FIG. 14 shows another embodiment of a bone screw with a plurality of side openings.

In FIG. 14, another embodiment with a plurality of side openings in the distal section 13 is shown. The side openings (101-106) are oriented into varying directions to allow for complete surrounding penetration of the material into the bone.

Figure 15:
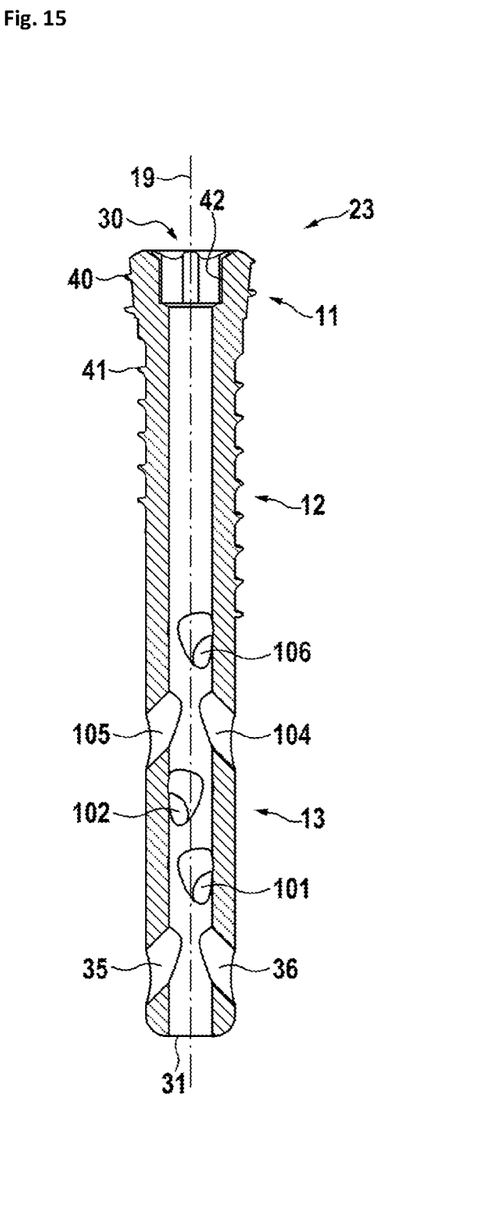
FIG. 15 shows a sectional view of the previous embodiment.

In FIG. 15, the above embodiment is shown in a sectional view. Here some pairs of opposing side openings (35, 46; 105, 104) are shown.

In FIG. 16, a humerus head 100 is shown with a bone plate 150 attached by the bone screws 10 and standard bone screws 110.

In this example, there is a fracture of the humerus head, which requires the use of bone screws 10, having a lumen and delivering cement through the lumen of the bone screws 10 to further stabilize the fractured humerus head. The bone shaft is not fractured, therefore regular screws 110 may be used to further hold the bone plate 150 to the bone 100.

It will be appreciated to those skilled in the art having the benefit of this disclosure that this disclosure is believed to provide bone screws and a method for treating a humerus fracture. Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as the presently preferred embodiments. Elements and materials may be substituted for those illustrated and described herein, parts and processes may be reversed, and certain features of the disclosure may be utilized independently, all as would be apparent to one skilled in the art after having the benefit of this description of the disclosure. Changes may be made in the elements described herein without departing from the spirit and scope of the disclosure as described in the following claims.

What is claimed is:

1. A bone screw, comprising:
    a proximal section including a first outer thread;
    a center section including a second outer thread;
    an unthreaded distal section on an opposite side of said center section from said proximal section;
    a channel extending from said proximal section to a distal opening of said unthreaded distal section; and
    at least one side opening extending from said channel to an outer surface of said unthreaded distal section, said at least one side opening including a cutting edge configured to cut a material as the bone screw is rotated in a direction for removing the bone screw.

2. The bone screw as recited in claim 1, wherein said cutting edge extends at an angle of less than 90 degrees relative to a longitudinal axis of the bone screw.

3. The bone screw as recited in claim 2, wherein said angle is defined between a tangent to an inner wall of said channel and an edge of said at least one side opening.

4. The bone screw as recited in claim 1, wherein a center axis of said at least one side opening is offset relative to a center axis of the channel, such that the center axis of said at least one side opening does not cross the center axis of the channel.

5. The bone screw as recited in claim 1, wherein said at least one side opening includes a diameter that increases in a direction from said channel toward said outer surface of said unthreaded distal section.

6. The bone screw as recited in claim 1, wherein said at least one side opening includes a first side opening having a first cutting edge on a first side of said channel and a second side opening having a second cutting edge on a second side of said channel.

7. The bone screw as recited in claim 6, wherein a sum of cross-sections of said first side opening and said second side opening exceeds a cross-section of said channel.

8. The bone screw as recited in claim 1, wherein said at least one side opening is oriented distally.

9. The bone screw as recited in claim 1, comprising a second side opening disposed in said center section.

10. The bone screw as recited in claim 1, wherein said unthreaded distal section includes a first portion proximal to said at least one side opening and a second portion distal to said at least one side opening, and both said first portion and said second portion are unthreaded.

11. The bone screw as recited in claim 1, wherein said at least one side opening includes an elliptical shape.

12. The bone screw as recited in claim 1, wherein a distal edge of said at least one side opening is proximal to said distal opening of said unthreaded distal section.

13. The bone screw as recited in claim 1, wherein a first pitch of said first outer thread is less than a second pitch of said second outer thread.

14. A bone screw, comprising:
    a proximal section;
    a center section;
    an unthreaded distal section on an opposite side of said center section from said proximal section;
    a channel extending through said proximal section, said center section, and said unthreaded distal section; and
    a side opening formed in at least one of said center section and said unthreaded distal section and including a diameter that increases in a direction from said channel toward an outer surface of said center section or said unthread distal section, said side opening including a cutting edge configured to cut a material as the bone screw is rotated in a direction for removing the bone screw.

15. The bone screw as recited in claim 14, wherein said side opening includes a cutting edge configured to cut a material as the bone screw is rotated in a direction for removing the bone screw.

16. The bone screw as recited in claim 14, wherein said side opening includes a first cutting edge on a first side of said channel and comprising a second side opening having a second cutting edge on a second side of said channel.

17. The bone screw as recited in claim 14, wherein said side opening is formed in said unthreaded distal section and comprising a second side opening formed in said center section.

18. The bone screw as recited in claim 14, wherein said side opening includes a conical or an elliptical shape.

19. The bone screw as recited in claim 14, wherein said side opening is oriented distally and includes a first center axis that does not cross a second center axis of said channel.

* * * * *